United States Patent
Nowak et al.

(10) Patent No.: US 8,524,257 B2
(45) Date of Patent: Sep. 3, 2013

(54) MENTHOL-CONTAINING SOLIDS COMPOSITION

(75) Inventors: Reinhard Nowak, Mt. Pleasant, SC (US); Michael Michler, Eimen (DE); Ingo Reiss, Holzminden (DE); Robert Winkel, Wuppertal (DE)

(73) Assignee: Symrise AG, Holzminden (DE)

( * ) Notice: Subject to any disclaimer, the term of this patent is extended or adjusted under 35 U.S.C. 154(b) by 1276 days.

(21) Appl. No.: 11/908,653

(22) PCT Filed: Mar. 9, 2006

(86) PCT No.: PCT/EP2006/060584
§ 371 (c)(1),
(2), (4) Date: Mar. 21, 2008

(87) PCT Pub. No.: WO2006/097427
PCT Pub. Date: Sep. 21, 2006

(65) Prior Publication Data
US 2008/0279947 A1     Nov. 13, 2008

Related U.S. Application Data

(60) Provisional application No. 60/662,534, filed on Mar. 16, 2005.

(51) Int. Cl.
*A61K 8/02* (2006.01)
*A61K 9/14* (2006.01)

(52) U.S. Cl.
USPC .............................. 424/401; 424/489; 426/96

(58) Field of Classification Search
USPC .................................... 424/489, 401; 426/96
See application file for complete search history.

(56) References Cited

U.S. PATENT DOCUMENTS

| 3,687,691 A | | 8/1972 | Adelstein |
| 4,011,270 A | * | 3/1977 | Carrington .................... 568/829 |
| 4,452,821 A | | 6/1984 | Gergely |
| 4,689,235 A | * | 8/1987 | Barnes et al. .................. 426/89 |
| 4,734,478 A | * | 3/1988 | Tsubakimoto et al. ....... 527/300 |
| 6,086,854 A | | 7/2000 | Arnold |
| 2003/0003059 A1 | | 1/2003 | Dana |
| 2003/0190296 A1 | | 10/2003 | Aronson |

FOREIGN PATENT DOCUMENTS

| AU | 729826 | | 2/2001 |
| EP | 0870493 | | 10/1998 |
| JP | 61161213 | | 7/1986 |
| JP | 08-020549 | * | 1/1996 |
| JP | 2001233758 | | 8/2001 |
| WO | WO0180671 | | 10/2003 |
| WO | WO2005026048 | | 3/2005 |

* cited by examiner

*Primary Examiner* — Lezah Roberts
*Assistant Examiner* — Tracy Liu
(74) *Attorney, Agent, or Firm* — Duane Morris LLP; J. Rodman Steele, Jr.; Gregory M. Lefkowitz

(57) ABSTRACT

A menthol-containing solids composition comprising or consisting of
(a) a solid menthol component consisting of bodies having a content of 95 wt. % or more menthol, based on the total weight of the bodies, and
(b) a solid silicon dioxide component comprising or consisting of particles having a particle size of not more than 100 μm,
wherein particles of the silicon dioxide component adhere to the surface of the bodies of the menthol component and wherein
the amount of the silicon dioxide component is not more than 4 wt. % and the amount of the menthol component is at least 95 wt. %, in each case based on the total weight of the solids composition.

17 Claims, No Drawings

MENTHOL-CONTAINING SOLIDS COMPOSITION

FIELD OF THE INVENTION

The invention relates to a menthol-containing solids composition, to articles comprising such a solids composition, to the use of such a solids composition and to a process for its preparation.

The menthol-containing solids composition is preferably free-flowing.

BACKGROUND OF THE INVENTION

L-Menthol has a unique refreshing taste, a minty odour and a pronounced cooling effect on the skin and mucosa. It is used, for example, in oral care, in cosmetic and pharmaceutical preparations, in tobacco and in confectionery, as described, for example, in Perfumer & Flavorist, Vol. 13, October-November 1988, p. 37.

L-Menthol is the main constituent of the peppermint oils from Mentha arvensis (content: 70 to 80%) and Mentha piperita (content: 50 to 60%). L-Menthol is obtained from the crude peppermint oil by crystallisation. Depending on the crystallisation method and the starting material, the crystals differ in terms of taste and also in terms of the size and shape of the crystals (Perfumer & Flavorist; Vol. 22, November-December 1997, p. 1). A small residual amount of liquid peppermint oil adheres to these menthol crystals obtained from peppermint oils (the content of l-menthol is conventionally not more than 99.2 wt. %) and inhibits caking or clumping of the menthol crystals, but also has a marked influence on the sensory profile.

Many processes for the preparation of synthetic menthol are known. An economic process for the preparation of synthetic l-menthol uses thymol, for example, as starting material. From the eight stereoisomeric menthols formed by hydrogenation, l-menthol is obtained via a plurality of process steps in a chemical purity of >99% and an enantiomeric purity of >99% (e.g. in Bauer, Garbe, Surburg, Common Fragrance and Flavor Materials, 4$^{th}$ Ed., Wiley-VCH, Weinheim 2001, p. 52-55). The l-menthol resulting from this process is distinguished in sensory terms by its purity and intensity.

Menthol, in particular l-menthol, is commercially available in various solid forms; powders, crystals, solidified distillate, flakes and pressed articles, for example, are conventional.

Synthetic l-menthol (having a melting point of from 42 to 43° C.) prepared and crystallised according to the processes from DE-A 2109456, DE-A 2530481 and EP 0 909 205 is available commercially in the form of white crystals or in the form of pressed articles (pellets) as well as in the form of a solidified distillate (Symrise GmbH & Co. KG, Holzminden).

Solid forms of menthol, in particular of peppermint-oil-free menthol, known hitherto form clumps after a prolonged time during storage, which impairs their pourability and handling ability.

In U.S. Pat. No. 3,064,311, l-menthol in flake form is described. For its preparation, distilled l-menthol is melted, and a thin, molten film layer is applied to a supercooled surface. The solidified l-menthol film is broken into small pieces. The product of this process is a brittle l-menthol flake which has a thickness of from 0.125 to 1.25 mm and a spread of from 3 to 25 mm. The flaked l-menthol so prepared exhibits adhesion and clumping of the flakes after 24 hours, as described in the US specification.

WO 03/101924 describes menthol pressed articles which have a content of alpha-menthol of greater than or equal to 70 wt. % and exhibit a comparatively very low tendency to caking or clumping. However, even these pressed articles gradually clump and cake together when stored for prolonged periods of over three months.

JP 08-020549 relates to l-menthol-containing powder comprising about 90 wt. % synthetic l-menthol (particle size from 50 to 200 μm) and about 10 wt. % silica gel (particle size less than 10 μm, preferably in the range from 2 to 5 μm). This product (bulk height: 50 cm) did not exhibit caking after one month's storage. For the preparation of the product, a surfactant (e.g. 2 wt. % decaglyceryl monolaurate, based on the total amount of menthol and silica gel) was first introduced into water at a temperature above the melting point of l-menthol (42° C.). Silica gel and molten menthol, or menthol on silica gel, were then introduced in succession into the mixture of water and surfactant at 50° C. After stirring for a short time, this mixture was cooled with ice-water, washed with water, filtered off and dried.

Our own tests have shown, however, that the product prepared according to JP 08-020549 exhibits a water content of up to 3 wt. % after drying. As already mentioned in the introduction to JP 08-020549, moisture leads to a lowering of the melting point of menthol and to a certain tendency to caking; the water content is accordingly disadvantageous. Furthermore, the residual content of surfactant in the described powdered, menthol-containing product is undesirable. In addition, the high content of silica gel in the disclosed menthol-silica gel powder is disadvantageous; inter alia, the silica gel imparts an unpleasant sensory impression in the mouth.

SUMMARY OF THE INVENTION

The object of the present invention was to provide a solids composition having a high content of menthol, wherein the composition should possess improved, very high storage stability, should be simple to prepare and easy to handle and, preferably, should have good ("free-flowing") pourability, making it readily processable.

This object has been achieved according to the invention by a menthol-containing solids composition comprising or (preferably) consisting of
(a) a solid menthol component consisting of bodies having a content of 95 wt. % or more menthol, based on the total weight of the bodies, and
(b) a solid silicon dioxide component comprising or (preferably) consisting of particles having a particle size of not more than 100 μm,
wherein the particles of the silicon dioxide component adhere to the surface of the bodies of the menthol component and wherein
the amount of the silicon dioxide component is not more than 4 wt. % and the amount of the menthol component is at least 95 wt. % (preferably at least 96 wt. %), in each case based on the total weight of the solids composition.

The menthol-containing solids composition according to the invention is preferably a free-flowing composition.

In the present text, any reference to the presence of a material in the solid state of aggregation ("solids composition", "solid component", "solid form" or the like) refers to the state at 20° C. and 1013 mbar. The same applies to references to "free-flowing" compositions.

DETAILED DESCRIPTION OF THE INVENTION

The invention is based on the surprising finding that it is possible to prepare a menthol-containing solids composition which has a high content of menthol and which possesses extremely high storage stability, that is to say high resistance to clumping and caking, by mixing a corresponding menthol component with a silicon dioxide component. The silicon dioxide component must comprise (silicon dioxide) particles having a particle size of not more than 100 µm or consist of such particles. Particles of the silicon dioxide component (b) adhere to the surface of the bodies of the menthol component.

In view of the very complex form of the process according to JP 08-020549 (see above), it is particularly surprising that the addition of silicon dioxide to a solid menthol component is able to prevent clumping and caking thereof over very long periods of much more than one month, or at least is able to inhibit clumping and caking thereof to such an extent that its use is not impaired.

Although silicon dioxide is already known as an anti-caking agent, this does not yet qualify silicon dioxide for use according to the invention. Our own tests have shown that it is not possible simply to use any conventional anti-caking agent in order to achieve the object underlying the invention. For example, menthol-containing solids compositions that comprised, instead of the silicon dioxide component (b) according to the invention, in each case 4 wt. %, based on the total weight of the solids composition, of other anti-caking agents (such as, for example, aluminium silicate, bentonite, calcium carbonate, sodium carbonate, sodium silicate, cellulose) proved to be unstable to storage.

The precise reason for the success according to the invention when using the above-mentioned silicon dioxide component (b) is not known in detail. Presumably, however, there is a particular, unexpected interaction between menthol and silicon dioxide which allows the silicon dioxide component (b) present according to the invention to adhere to the surface of the bodies of the menthol component to such an extent that the sublimation capacity or evaporation of the menthol is reduced for a long time afterwards. Our own investigations have shown that the caking and clumping of conventional forms of menthol are greatly furthered by the sublimation or evaporation and re-precipitation of the menthol. Apparently, silicon dioxide particles having a particle size of not more than 100 µm, preferably not more than 50 µm and particularly preferably not more than 20 µm, are excellently suitable for adhering to the surface of bodies of the menthol component and limiting for a long time afterwards the "free" menthol surface area available for sublimation or evaporation. For preferred types of silicon dioxide component (b) see below.

The menthol-containing solids composition according to the invention is preferably in such a form that particles of the silicon dioxide component adhere to and cover the surface of the bodies of the menthol component in such a manner that the sublimation capacity or evaporation of the menthol from the bodies of the menthol component at 25° C. and 1013 mbar is reduced by at least 25%, preferably at least 40%, compared with the menthol component (a). This reduction in the rate of sublimation or rate of evaporation can be determined, for example, by means of thermogravimetry in accordance with DIN 51006. In thermogravimetry, in the present case the mass of the unmixed menthol component (a) or of a menthol-containing solids composition according to the invention is measured at the same constant temperature (i.e. isothermally) below the melting point, preferably at 25° C. (and at 1013 mbar), as a function of time.

Our own microscope pictures have shown that in preferred menthol-containing solids compositions according to the invention, at least 80%, preferably at least 90% and particularly preferably at least 95%, of the surface of the solid menthol component (a) is covered with the solid silicon dioxide component (b).

A process according to the invention for the preparation of a menthol-containing solids composition according to the invention is very simple to carry out, in particular in comparison with the form of the process according to JP 08-020549. It comprises the following steps:
mixing
(a) a solid menthol component consisting of bodies having a content of 95 wt. % or more menthol, based on the total weight of the bodies, and
(b) a solid silicon dioxide component comprising or consisting of particles having a particle size of not more than 100 µm, until particles of the silicon dioxide component adhere to the surface of the bodies of the menthol component,
wherein
the amount of the silicon dioxide component is not more than 4 wt. % and the amount of the menthol component is at least 95 wt. %, in each case based on the total weight of the prepared solids composition.

The solid menthol component used according to the invention consists of bodies having a content of 95 wt. % or more menthol, based on the total weight of the bodies. However, the menthol content is preferably greater than or equal to 98 wt. %; very particular preference is given to a menthol content of greater than or equal to 99 wt. %, and a menthol content of greater than or equal to 99.5 wt. % is particularly preferred, in each case based on the total weight of the bodies of the solid menthol component.

It is evident from the above that the bodies of the menthol component do not usually comprise any inorganic constituents, that is to say in particular no water and also no silicon dioxide; this distinguishes the bodies of the menthol component present according to the invention from the menthol particles contained in the l-menthol-containing powder according to JP 08-020549 which, in addition to comprising surfactant residues, comprise a considerable amount of water and also, as a result of the process, silica gel particles in their insides.

In some cases, however, the presence of small amounts of inorganic constituents in the bodies of the menthol component present according to the invention can be acceptable or even desirable. Preferably, the content of inorganic constituents is then in the range from 0 to 1%, based on the total weight of the bodies. In a particularly preferred embodiment, the menthol-containing solids composition according to the invention comprises not more than 0.2 wt. % water, based on the total weight of the solids composition.

The form of the bodies of the menthol component (a) in a menthol-containing solids composition according to the invention can be varied within wide limits. In particular, the bodies of the menthol component can be present in the form of crystals, prills, flakes, pressed articles, pastilles, granules, powder and/or dust. Particular mention is to be made of those forms which have a particularly pronounced caking tendency in the absence of the silicon dioxide component (b) present according to the invention, that is to say menthol bodies in the form of crystals, prills or flakes.

The menthol-containing solids compositions according to the invention are extraordinarily stable to storage and are still flowable even after long periods. Even after a storage period of more than 12 months at 20° C. and a layer height of 1 m, no caking or clumping was detectable in our own investigations. In those investigations, a solid menthol component consisting of bodies in the form of crystals or pellets was used. The menthol-containing solids composition according to the invention that was studied could be handled comfortably and safely throughout the entire period of observation and remained pourable, flowable and meterable.

Particularly preferred menthol-containing solids compositions according to the invention contain (i) no peppermint oil on the surface of the bodies of the menthol component (in contrast to conventional menthol products isolated from naturally occurring mixtures) and/or (ii) no surfactants, that is to say no surface-active substances, and/or (iii) not more than 0.2 wt. % water, based on the total weight of the solids composition (in contrast to the products according to JP 08-020549).

The menthol used in the menthol-containing solids composition according to the invention can be d-menthol, l-menthol or any desired mixture thereof, preference being given to l-menthol, d-menthol and racemic menthol, and particular preference being given to l-menthol.

The menthol used can be of synthetic or natural origin, but the use of synthetic menthol is preferred. When using menthol of natural origin, it is particularly difficult to ensure the high purity of the menthol that is often desired (see the information given above).

It is also possible to use any desired mixtures of synthetic and natural menthol and of racemic and enantiomerically pure menthol.

If menthol crystals, preferably needle-shaped crystals, are used as the menthol component, they preferably have crystal sizes of up to 2 mm, with crystal sizes in the range from 50 to 1500 μm being preferred. Particularly preferably, more than 75 wt. % of the crystals have a crystal size in the range from 50 to 1000 μm (1 mm), of which preferably more than 60 wt. % of the crystals have a crystal size in the range from 200 to 800 μm (0.2 to 0.8 mm), the amounts being based in each case on the total weight of the menthol crystals.

A typical crystal size distribution (by sieve analysis) of menthol crystals that are particularly preferably used in the preparation of a menthol-containing solids composition according to the invention is the following:
from 2 to 25 wt. % having a crystal size below 0.20 mm;
from 40 to 80 wt. % having a crystal size in the range from 0.20 mm to 0.50 mm;
from 5 to 35 wt. % having a crystal size in the range from 0.51 mm to 0.80 mm;
from 1 to 15 wt. % having a crystal size in the range from 0.81 mm to 1.0 mm;
from 0.2 to 8 wt. % having a crystal size in the range from 1.1 mm to 1.25 mm; and
from 0.2 to 10 wt. % having a crystal size in the range from 1.26 mm to 2 mm.

In the preparation of a menthol-containing solids composition according to the invention, a change in the crystal size and crystal size distribution can occur, mainly when menthol crystals, in particular needle-shaped menthol crystals, are used. Depending on the nature and type of the mixer used and on the mixing intensity and mixing time, a menthol-containing solids composition is obtained in which the menthol crystals are smaller overall than those originally used prior to the mixing operation.

As already mentioned, the bodies of the menthol component can be in many different forms, in addition to the crystalline form, for example in the form of prills, flakes, pressed articles, pastilles, granules, powder and/or dust.

Prills are small spheres having a diameter in the range from 0.2 to 1.5 mm, preferably in the range from 0.3 to 1 mm. Prills are obtained, for example, by forming drops of liquid menthol and then cooling the menthol drops in a cooling medium (e.g. cold air).

Flakes are obtained, for example, by solidifying a menthol melt on a cooling roller. These flakes usually have a flake thickness of from 0.5 to 2 mm, the flake surface is variable. Normally, the flake surface is in the range length: from 5 to 15 mm, width: from 2 to 10 mm.

Pressed articles can be in the form of, for example, spheres, cubes, parallelepipeds, cushion-shaped articles, cylinders, tablets, pellets or briquettes. Pressing (compacting) of the menthol can be carried out by a very wide variety of methods. Proven pressing methods are described, for example, in Chemie–Anlagen+Verfahren 1985, issue 4, pages 51, 54 and 59. The dimensions of the pressed articles can vary greatly. In the case of a sphere, the diameter is in the range from 1 mm to 40 mm, preferably in the range from 5 to 20 mm. In the case of a pellet, the length and width are in the range from 3 to 30 mm, preferably in the range from 5 to 15 mm. The height is in the range from 0.5 to 20 mm, preferably in the range from 2 to 8 mm.

During compacting, a pressing force in the range from 5 to 200 kN (kilo-Newtons) is usually applied in the compacting device. Preference is given to a pressing force of from 10 to 100 kN, particularly preferably from 20 to 80 kN. During the compacting of the menthol, preference is given to linear pressing forces of from 1 to 5 Newtons/mm·mm, based on the diameter.

Within the scope of the present text, pastilles are understood as being menthol forms obtained by dripping a menthol melt onto a cooled, not curved cooling surface (e.g. cooling belt, cooling plate).

Granules are, for example, menthol forms which are obtainable by breaking or other types of fragmenting and which accordingly can be very different in terms of form and size (e.g. broken granules).

Powder and dust of menthol are obtained, for example, either as a by-product in the crystallisation of natural l-menthol or can be a constituent in products obtained by grinding larger menthol bodies.

According to the invention, the amount of the silicon dioxide component is not more than 4 wt. %, based on the total weight of the solids composition. Preferably, the amount of the silicon dioxide component is not more than 2.5 wt. %, but it is preferably in the range from 0.2 to 2 wt. %, based on the total weight of the solids composition.

In a menthol-containing solids composition according to the invention, the amount of the menthol component is at least 95 wt. %, based on the total weight of the solids composition. However, the amount of the menthol component is particularly preferably in the range from 96 to 99.8 wt. %, very particularly preferably in the range from 98 to 99.8 wt. %.

It has already been stated above that silicon dioxide is far more suitable than other substances for covering the surface of menthol bodies so that the sublimation capacity or vapour pressure of the menthol bodies is reduced. It will therefore be understood that the preferred amount of the silicon dioxide component in a menthol-containing solids composition according to the invention is dependent on the form in which the bodies of the menthol component are present because, depending on the form of the bodies, different values of the ratio of the surface area of the bodies to the weight of the bodies are obtained.

A menthol-containing solids composition according to the invention having a menthol component consisting of menthol crystals preferably contains from 0.5 to 2.5 wt. %, more preferably from 0.5 to 2.0 wt. %, of a silicon dioxide component (b).

A menthol-containing solids composition according to the invention in which the menthol component (a) consists of menthol pressed articles or menthol flakes preferably comprises from 0.2 to 1 wt. % of a silicon dioxide component (b).

A menthol-containing solids composition according to the invention having a menthol component consisting of menthol prills preferably comprises from 0.3 to 1.5 wt. % of a silicon dioxide component (b).

The particles of the silicon dioxide component of a menthol-containing solids composition according to the invention preferably consist of precipitated silica and/or pyrogenic silicon dioxide. The use of pyrogenic silicon dioxide is slightly preferred over that of precipitated silica.

Preference is given to the use of (preferably pyrogenic) silicon dioxide having a specific surface area in the range from 50 to 500 $m^2/g$, preferably in the range from 100 to 400 $m^2/g$ (surface area according to BET, in accordance with DIN 66131).

Precipitated silicas (empirical formula: $SiO_2$) can be prepared, for example, by means of precipitation processes or hydrothermal processes and are obtainable in various grades from Degussa-Hüls AG, inter alia, under the trade names Sipernat® or Carplex®. Precipitated silicas advantageously have a specific surface area in the range from 50 to 500 $m^2/g$ according to BET and particle sizes in the range from 3 to 100 μm. Preferred precipitated silicas are amorphous and have particle sizes in the range from 3 to 50 μm.

Amorphous, highly dispersed pyrogenic silicon dioxide can be prepared, for example, by means of an oxyhydrogen flame or in an electric arc. Highly dispersed hydrophobic or hydrophilic silicon dioxides are obtainable in various grades from Degussa-Hüls AG, for example, under the trade name Aerosil®. The size of the spherical primary particles is generally in the range from 7 to 40 nm. These primary particles form agglomerates and aggregates (see DIN 53206) and, in contrast to precipitated silicas, do not exhibit a defined agglomerate size. Preferably, the highly dispersed silicon dioxide has a specific surface area in the range from 50 to 400 $m^2/g$, preferably in the range from 100 to 300 $m^2/g$, according to BET. The mean size of the primary particles is preferably in the range from 7 to 20 nm, more preferably in the range from 7 to 16 nm.

The pyrogenic silicon dioxides exhibit a loss on drying of not more than 2 wt. % after 2 hours at 105° C. (in accordance with DIN ISO 787/II). After 2 hours' annealing at 1000° C., the pyrogenic silicon dioxides exhibit an $SiO_2$ content of at least 99.8 wt. %. The sieve residue (according to Mocker, 45 μm; in accordance with DIN ISO 787/XVIII) is less than 0.1 wt. %.

The silanol groups present on the particle surface can be free (hydrophilic silicon dioxide) or derivatised by silanes or silazanes (hydrophobic silicon dioxide).

Further information on silicon dioxides which can be used within the scope of the invention can be found, for example, in EP 0 331 425 and the Sivento product brochure "Aerosil®—Pyrogene Kieselsauren" of Degussa-Hüls AG.

The menthol-containing solids compositions according to the invention possess outstanding flowability even after a long storage time.

The flowability of a bulk material can be characterised by the angle of repose. With an angle of repose of less than 30°, a material is said to be "very readily flowable", with an angle of repose in the range from 30° to 45° it is "free-flowing", and with an angle of repose of greater than 45° it is "poorly flowable". It is to be noted that no angle of repose at all can be determined in the case of heavily clumped or caked forms, because in such cases there is no flowability. The angle of repose can be determined according to DIN ISO 4324.

Preference is given to menthol-containing solids compositions according to the invention in which the silicon dioxide component and the menthol component are so selected and the amounts thereof are so matched to one another that the solids composition is "very readily flowable" or at least "free-flowing".

Surprisingly, the menthol-containing solids compositions according to the invention also contribute towards solving a further problem which is of great importance in practice. Hitherto, products containing menthol in high concentrations had the disadvantage that the menthol crystallises out of or in such products. Ready-to-use liquid flavouring compositions having a high menthol content, in particular for use in the field of oral care, are prepared, for example, by mixing up to 50 wt. % solid menthol with liquid peppermint oils. The solid menthol is incorporated into the flavouring composition to enhance the fresh, menthol-like taste impression and is thereby dissolved (e.g. in liquid peppermint oil). It was a problem hitherto that during storage at relatively low temperatures and/or during storage for a relatively long period, menthol crystallises out of such flavouring compositions having a high menthol content, so that a heterogeneous product forms. The sensory impression, inter alia, of such products changes adversely as a result. Surprisingly, in products into which a menthol-containing solids composition according to the invention has been incorporated, there is only a very slight tendency, or even no tendency at all, for the menthol to crystallise out; in respect of the menthol constituent of such products, it is accordingly possible, when using the menthol-containing solids composition according to the invention, to achieve increased storage stability. In that case, the bodies of the menthol component of the menthol-containing solids composition according to the invention are preferably in the form of crystals.

Menthol-containing solids compositions according to the invention, in particular those in which the bodies of the menthol component are in the form of crystals, dissolve rapidly in water, ethanol and mixtures thereof, even without the additional supply of heat (see Example 2). The solids compositions according to the invention can accordingly be incorporated directly into a product without having to be diluted or dissolved beforehand. The rapid solubility is advantageous inter alia if rapid distribution and/or dissolution of the menthol is desirable or necessary, such as, for example, in the preparation of flavourings, chewing gums, sweets or toothpastes. Accordingly, it is possible when preparing products to incorporate the menthol-containing solids composition according to the invention into a product separately from the rest of the flavouring and as a result reduce the times required for mixing or kneading. For example, in the preparation of a ready-to-use toothpaste containing 1 wt. % of a toothpaste flavouring which in turn comprises 40 wt. % solid menthol, the measured amount of the toothpaste flavouring without solid menthol can be reduced to 0.6 wt. % and an amount of 0.4 wt. % in the form of a menthol-containing solids composition according to the invention can be added directly to the toothpaste mixture.

A menthol-containing solids composition according to the invention additionally exhibits unexpected sensory effects.

In chewing gum strips/dragées, in comparison with the incorporation of conventional l-menthol crystals, the incorporation of a menthol-containing solids composition according to the invention in the same measured amount (1 wt. %, based on the finished chewing gum) brought about delayed release of the flavour on chewing and accordingly an increased "long-lasting" effect, which means that the flavour is perceived for longer in terms of taste. In addition, the flavour profile of chewing gums into which an amount of menthol-containing solids compositions according to the invention had been incorporated exhibited a clearer and more intense menthol taste in comparison.

A combination of the incorporation of (i) spray-dried menthol (e.g. 0.7 wt. %, based on a finished chewing gum), which provides a balanced fresh and rapid impact, and (ii) the menthol-containing solids composition according to the invention (e.g. 0.7 wt. %, based on a finished chewing gum), which brings about the delayed release of the flavour and accordingly the strong "long-lasting" effect, is accordingly an ideal, mutually complementary combination which covers the entire taste spectrum, in particular in the case of chewing gum strips/dragées.

When (a) a peppermint flavouring, for example a commercially available Optamint® flavouring (Symrise GmbH & Co. KG), and (b) a menthol-containing solids composition according to the invention are incorporated in combination into chewing gum strips/dragées, a strong, pronounced "long-lasting" effect is to be perceived in this case too.

In the case of dragées, in particular chewing gum dragées, the taste can be markedly improved if the coating (i.e. the coating, which is sometimes multi-layered, applied by means of sugar coating) is prepared using a menthol-containing solids composition according to the invention. When they are chewed, corresponding dragées according to the invention produce in the mouth a new type of fresh menthol taste which is very clear and intense. This sensory effect is also achieved when other confectionery, such as, for example, chewy sweets or hard caramels, is made into dragées.

A coating preferably comprises at least one sugar (preferably selected from xylose, fructose, galactose, glucose, mannose, lactose, maltose, sucrose and mixtures thereof, particular preference being given to glucose and sucrose) and/or at least one sugar substitute (preferably selected from isomalt, sorbitol, xylitol, maltitol and/or mannitol).

The present invention accordingly relates in a further aspect to a sugar-coated product suitable for consumption, characterised in that the coating comprises (a) solid menthol bodies and (b) a solid silicon dioxide component comprising or (preferably) consisting of particles having a particle size of not more than 100 μm, wherein in at least one layer of the coating the amount of the silicon dioxide component is not more than 4 wt. %, based on the total weight of components (a) and (b).

The use of the menthol-containing solids compositions according to the invention in dragées and compressed products is very advantageous because, even with a measured amount of only 0.2 wt. %, the taste profile is much clearer and fresher than with the solid forms of menthol used hitherto. An intense menthol taste is produced, which increases in an outstanding manner to a "power mint" product if the measured amount is increased to 0.5 wt. %. The percentages are based on the total weight of the ready-to-use dragées or compressed products. In dragées and compressed products, the menthol-containing solids compositions according to the invention effect more freshness, or an intensification of the fresh taste, compared with other forms of administration in the same measured amount.

The menthol-containing solids compositions according to the invention permit the preparation of glassy flavouring particles by means of the extrusion of a flavoured matrix of sugar(s) and/or sugar substitute(s) having a content of menthol that was hitherto impossible. The preparation and use of glassy flavouring particles is described, for example, in WO 03/092412 and the literature cited therein. Hitherto, solid menthol has been dissolved in a solvent and introduced into the extrusion process in the form of a solution. The maximum achievable menthol concentration in the finished glassy flavouring particles is thereby determined by two limits: on the one hand by the solubility limit of the menthol in the solvent(s) used, and on the other hand by the amount of solvent(s) used, because solvents, on account of their softening properties, reduce the extrudability of the flavoured matrix of sugars and/or sugar substitutes or, in too large an amount, prevent extrusion.

According to the invention it is now possible to prepare a solid (homogeneous) pre-mixture of sugar(s) and/or sugar substitute(s) and menthol-containing solids composition according to the invention, which pre-mixture can be extruded directly, as a result of which menthol contents of up to 20 wt. % can be achieved, based on the finished glassy flavouring particles. This corresponds to a menthol content that is 5 to 6 times greater than that hitherto possible in glassy flavouring particles.

In a further aspect, therefore, the present invention relates to glassy flavouring particles comprising at least 3.5 wt. %, preferably at least 5 wt. %, menthol, based on the finished glassy flavouring particles, as well as a solid silicon dioxide component. In preferred embodiments, the content of silicon dioxide in a glassy flavouring particle according to the invention is at least 0.05 wt. %, preferably at least 0.1 wt. %.

Of course, the menthol-containing solids composition according to the invention can also be used for purposes other than those listed above by way of example.

Accordingly, the present invention relates very generally also to articles that comprise a menthol-containing solids composition according to the invention. However, the articles are preferably selected from the group consisting of: products suitable for consumption, smoking products, tobacco products, perfumes (fragrance mixtures), flavouring mixtures, oral hygiene products, cosmetic, pharmaceutical and dermatological products, encapsulated menthol-containing solids compositions.

Accordingly, a related aspect of the present invention relates to the use of a menthol-containing solids composition according to the invention in the preparation of a menthol-containing article, in particular an article selected from the group consisting of: products suitable for consumption, smoking products, tobacco products, perfumes (fragrance mixtures), flavouring mixtures, oral hygiene products, cosmetic, pharmaceutical and dermatological products, encapsulated menthol-containing solids compositions.

Naturally, the menthol-containing solids compositions according to the invention are used in particular for flavouring or fragrancing the mentioned articles.

The content of the menthol-containing solids composition according to the invention in a product varies considerably according to the product type:

In ready-to-use products, such as, for example, oral hygiene products, products suitable for consumption (e.g. foodstuffs) or cosmetic products, the content of the menthol-containing solids composition according to the invention is preferably in the range from 0.01 to 10 wt. %, particularly preferably in the range from 0.1 to 5 wt. %, based on the total weight of the ready-to-use product.

In flavourings or fragrance mixtures, on the other hand, the content of the menthol-containing solids composition according to the invention can be very much higher and is generally in the range from 0.01 to 70 wt. %, preferably in the range from 1 to 50 wt. %, based on the total weight of the flavouring or fragrance mixture.

A product suitable for consumption is a product that is intended to be introduced into the human oral cavity, to remain there for a particular time and then to be either swallowed, that is to say consumed (e.g. foodstuffs), or removed from the mouth again (e.g. chewing gums). Also included are all substances or products which are intended to be ingested by humans in the processed, partially processed or unprocessed state. Further included are all substances that are added to the product suitable for consumption during its preparation, processing or treatment.

Preferred products suitable for consumption are, for example, baked goods (biscuits, cakes, muffins, waffles, baking mixtures), sugar products (hard caramels, soft caramels, chewy sweets, compressed products, dragées, sugar pearls, sugar fillings), milk products (yoghurts, puddings, ice cream), chocolate products (white, milk or dark chocolate, chocolate bars), fatty substances (fillings for baked goods, such as, for example, fillings for biscuits, fatty fillings for chocolate, fatty fillings for bars), chewing gums (sugar-free, sugar-containing, strips, compressed products, dragées), snacks and snack mixtures, water-soluble powdered products, toppings.

An oral hygiene product (also referred to hereinbelow as an oral care product or oral hygiene preparation) within the scope of the invention is understood as being one of the formulations known to the person skilled in the art for cleaning and caring for the oral cavity and the pharynx and also for freshening the breath. Care of the teeth and gums is also expressly included herein. Forms of administration of conventional oral hygiene formulations are creams, gels, pastes, foams, emulsions, suspensions, aerosols, sprays, as well as capsules, granules, pastilles, tablets, sweets or chewing gums, it being understood that this list is not limiting for the purposes of this invention.

Preferred oral hygiene products are in particular tooth care agents, such as toothpastes, tooth creams, tooth gels, tooth powders, mouthwashes, dental floss, seamless capsules, sweets for sucking, and sugar-free chewing gums.

A menthol-containing solids composition according to the invention can also be processed further by encapsulation. Preferably, the menthol-containing solids composition and/or a liquid or solid preparation containing it is encapsulated with a solid encapuslating material which is preferably selected from starches, degraded or chemically or physically modified starches (in particular dextrins and maltodextrins), gelatins, gum arabic, agar-agar, ghatti gum, gellan gum, modified and unmodified celluloses, pullulan, curdlan, carrageenans, alginic acid, alginates, pectin, insulin, xanthan gum and mixtures of two or more of the mentioned substances.

The solid coating material is preferably selected from gelatins (porcine, bovine, poultry and/or fish gelatins and mixtures thereof are advantageous, preferably comprising at least one gelatin having a Bloom value of greater than or equal to 200, preferably having a Bloom value of greater than or equal to 240), maltodextrin (preferably obtained from maize, wheat, tapioca or potato, preferred maltodextrins have a DE value in the range from 10 to 20), modified cellulose (e.g. cellulose ether), alginates (e.g. Na alginate), carrageenan (beta-, iota-, lambda- and/or kappa-carrageenan), gum arabic, curdlan and/or agar-agar. Gelatins are preferably used in particular owing to their ready availability in different Bloom values.

For the purposes of oral hygiene, particular preference is given specifically to seamless gelatin or alginate capsules, the coating of which dissolves very rapidly in the mouth or bursts on chewing, thus releasing the active ingredient into the oral cavity. They can be prepared, for example, as described in EP 0 389 700, JP 7 196 478, U.S. Pat. No. 4,251,195, U.S. Pat. No. 6,214,376 WO 03/055587 or WO 2004/050069.

The cosmetic and/or dermatological products according to the invention can be composed in the conventional manner and be used for cosmetic and/or dermatological sun protection, also for the treatment, care and cleansing of the skin and/or hair and as a make-up product in decorative cosmetics. Accordingly, the products according to the invention, according to their composition, can be used, for example, as a skin protection cream, cleansing milk, sun protection lotion, nutrient cream, day or night cream, etc. It is optionally possible and advantageous to use the products according to the invention as a base for pharmaceutical products. Preference is given in particular to those cosmetic and dermatological products which are in the form of a skin care or make-up product. Typical forms are creams, gels, lotions, alcoholic and aqueous/alcoholic solutions, emulsions, or preparations in stick form. Such agents can also comprise as further auxiliary substances and additives mild surfactants, co-emulsifiers, superfatting agents, pearlescent waxes, consistency-imparting agents, thickeners, polymers, silicone compounds, fats, waxes, stabilisers, biogenic active ingredients, deodorant active ingredients, anti-dandruff agents, film-forming agents, swelling agents, hydrotopic agents, preservatives, insect repellents, tanning agents, artificial self-tanning agents (e.g. dihydroxyacetone), solubilisers, perfume oils, colourings, germ-inhibiting agents and the like.

For use, the cosmetic and dermatological products according to the invention are applied in a sufficient amount to the skin and/or hair in the manner conventional for cosmetics.

Particular preference is given to those cosmetic and/or dermatological products according to the invention which are in the form of a cosmetic agent for protecting the skin and hair. In addition to UV-A, UV-B and/or broad-band filters used according to the invention, such agents can contain at least one inorganic pigment, preferably an inorganic micropigment.

The cosmetic and/or dermatological products according to the invention can contain cosmetic auxiliary substances such as are conventionally used in such products, for example preservatives, bactericides, perfumes, substances for preventing foaming, colourings, pigments that have a colouring action, thickeners, moisturising substances and/or humectants, fats, oils, waxes or other conventional constituents of a cosmetic or dermatological product, such as alcohols, polyols, polymers, foam stabilisers, electrolytes, organic solvents or silicone derivatives.

Further preferred embodiments of the present invention will become apparent from the accompanying patent claims and the examples which follow. Unless indicated otherwise, amounts in the examples are based on weight.

Example 1

In Examples 1a and 1b below there was used synthetic l-menthol (ex-thymol) in the form of freshly prepared needle-shaped crystals (the content of menthol having a melting point of 42-43° C. was >99 wt. %) having the following crystal size distribution (sieve analysis):

13 wt. % having a crystal size below 0.20 mm;
58 wt. % having a crystal size in the range from 0.20 mm to 0.50 mm;
19 wt. % having a crystal size in the range from 0.51 mm to 0.80 mm;
5 wt. % having a crystal size in the range from 0.81 mm to 1.0 mm;
2 wt. % having a crystal size in the range from 1.1 mm to 1.25 mm; and 3 wt. % having a crystal size in the range greater than 1.25 mm.

Example 1a

L-menthol (25 kg) in the form of freshly prepared needle-shaped crystals (for particle distribution see Example 1) was placed in a mixer and mixed briefly and intensively with 380 g of pyrogenic silica (Aerosil® 200, mean size of the primary particles: 12 nm, surface area according to BET (in accordance with DIN 66131): 200±25 m²/g; obtainable from Degussa-Hüls AG). The content of pyrogenic silica (silicon dioxide component) in the total solids mixture was about 1.5%. The original menthol crystals were comminuted by the mixing operation.

The resulting menthol-containing solids composition according to the invention was subjected to sieve analysis and exhibited the following particle distribution:
49.6 wt. % having a crystal size below 0.20 mm;
45 wt. % having a crystal size in the range from 0.20 mm to 0.50 mm;
3.2 wt. % having a crystal size in the range from 0.51 mm to 0.80 mm;
2 wt. % having a crystal size in the range from 0.81 mm to 1.0 mm;
0.1 wt. % having a crystal size in the range from 1.1 mm to 1.25 mm; and
0.1 wt. % having a crystal size in the range greater than 1.25 mm.

This menthol-containing solids composition was packed in a plastics bag in a cube-shaped cardboard box and stored at 20° C. (bulk height: 50 cm). Every 14 days, the flowability of the composition according to the invention was tested visually and mechanically. No caking or clumping could be detected even after 12 months.

Example 1b

Over a period of one hour, 150-200 kg of l-menthol in the form of freshly prepared needle-shaped crystals (for particle distribution see Example 1) were fed via a vibrating trough to a compactor device (Hosokawa Bepex GmbH) consisting of two compactor rollers with profiled surfaces (circumference 60 cm, width 10 cm, surface area 600 cm²). At room temperature and with a pressing force of 50 kN, the compactor produced pressed articles in the form of pellets (cushion shape) having the dimensions length=width=10.2 mm and height=5 mm.

50 kg of these cushion-shaped pellets were mixed with 350 g of pyrogenic silica (Aerosil® 200, mean size of the primary particles: 12 nm, surface area according to BET (in accordance with DIN 66131): 200±25 m²/g; obtainable from Degussa-Hüls AG).

The menthol-containing preparation so prepared did not exhibit any clumping or caking even after a storage time of 12 months and a bulk height of 100 cm at room temperature.

Example 1c

L-Menthol (25 kg) in the form of freshly prepared needle-shaped crystals (for particle distribution see Example 1) was placed in a mixer and mixed briefly and intensively with different amounts of pyrogenic silica (Aerosil® 200, see Example 1a). The amount of pyrogenic silica (silicon dioxide component) in the total solids mixture was 0.5 wt. %, 1 wt. %, 2 wt. % or 4 wt. %. The original menthol crystals were comminuted by the mixing operation (see Example 1a). The menthol-containing solids compositions having different contents of silicon dioxide were each packed in a plastics bag in a cube-shaped cardboard box and stored at 20° C. (bulk height: 50 cm). After two months, no caking or clumping could be detected in any of the total of four compositions. The solids compositions still exhibited very good flowability even after two months.

Example 1d

Table 1 shows the results of a flowability test after three months' storage at 20° C. with menthol crystals (bulk height: 50 cm) having a particle size distribution according to Example 1a. The percentage contents of highly dispersed silicon dioxide in question are based on the menthol-containing composition consisting of menthol crystals and highly dispersed silicon dioxide.

TABLE 1

|  | 0.5 wt. % flow agent | 1 wt. % flow agent | 2 wt. % flow agent | 4 wt. % flow agent |
| --- | --- | --- | --- | --- |
| Aerosil ® 805 (150 m²/g; 12 nm), hydrophobic | B | B | A | A |
| Aerosil ® 812 (260 m²/g; 7 nm), rendered hydrophobic with trimethylsilyl groups | B | A | A | A |
| Aerosil ® 972 (110 m²/g; 16 nm), rendered hydrophobic with dimethylsilyl groups | B | A | A | A |
| Aerosil ® 150 (150 m²/g; 14 nm), hydrophilic | A | A | A | A |
| Aerosil ® 200 (200 m²/g; 12 nm), hydrophilic | A | A | A | A |
| Aerosil ® 300 (300 m²/g; 7 nm), hydrophilic | A | A | A | A |

The figures in brackets relate to the specific surface area in m²/g according to BET (in accordance with DIN 66131) and the mean size of the primary particles. The various Aerosil® grades are obtainable from Degussa-Hüls AG.
D=pronounced clumping, no flowability
C=moderate clumping, poor flowability
B=free flowability, scarcely any clumping
A=very good flowability, no clumping Example 2

The different rates of dissolution of a solids composition according to the invention of Example 1a above and of forms of l-menthol that are not in accordance with the invention were compared.

To this end, 5 g of l-menthol or 5 g of the l-menthol-containing solids composition according to the invention of Example 1a were added to 95 g of a mixture, kept at a constant temperature of 20° C., of equal parts by weight of ethanol and water, and the time taken for the menthol or the menthol-containing solids composition to dissolve completely (visual determination) was calculated.

The dissolving test was carried out in a glass beaker having a diameter of 5 cm and a filling height of 7 cm. The contents of the glass beaker were stirred during the dissolving test in each case using a magnetic stirring bead having a length of 4 cm with a magnetic stirrer speed of 4 revolutions per second. The temperature was monitored with a Pt-100 thermometer which was immersed to a depth of 5 cm in the liquid, was located at a distance of 1 cm from the wall of the glass beaker and at the same time served as flow breaker.

The crystals of natural menthol used in the dissolving test had a content of l-menthol of 99.2% and a content of menthol-free peppermint oil of 0.8% (amounts in GC percent by surface area). The size of the crystals corresponded to the typical (commercial) crystal geometry of natural l-menthol.

Table 2 below shows the dissolution times for the various forms of l-menthol that are not in accordance with the invention, in comparison with the menthol-containing solids composition from Example 1a.

TABLE 2

|  | Time to complete dissolution |
|---|---|
| Menthol pellets according to WO 03/101924, Example 1 | 504 sec |
| Crystals of natural menthol (rod-shaped crystals, length 15 to 20 mm, diameter 2 to 4 mm) | 255 sec |
| Menthol crystals from Example 1 | 170 sec |
| Clumped menthol crystals, obtained by storing the menthol crystals from Example 1 for 2 months | 280 sec |
| Menthol-containing composition according to the invention from Example 1a (1.5 wt. % SiO$_2$) | 58 sec |

Formulation Examples F1-F14

F1. Gel Tooth Cream

|  | I (%) | II (%) | III (%) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Peppermint oil flavouring | 0.90 | 0.56 | 0.30 |
| Menthol-containing composition from Example 1a | 0.125 | 0.50 | 0.90 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | ad 100.00 | ad 100.00 | ad 100.00 |

F2. Anti-Plaque Tooth Cream

|  | I (%) | II (%) | III (%) |
|---|---|---|---|
| Na carboxymethylcellulose | 1.00 | 1.00 | 1.00 |
| Glycerol | 12.50 | 12.50 | 12.50 |
| Sorbitol 70%, in water | 29.00 | 29.00 | 29.00 |
| Na saccharinate | 0.20 | 0.20 | 0.20 |
| Na fluoride | 0.22 | 0.22 | 0.22 |
| Azacycloheptane-2,2-diphospho acid, disodium salt | 1.00 | 1.00 | 1.00 |
| Bromochlorophene | 0.10 | 0.10 | 0.10 |
| Spearmint flavouring | 1.00 | 0.60 | 0.20 |
| Menthol-containing composition from Example 1a | 0.125 | 0.56 | 1.00 |
| Abrasive silica | 15.00 | 15.00 | 15.00 |
| Thickening silica | 5.00 | 5.00 | 5.00 |
| Sodium dodecyl sulfate (SDS) | 1.50 | 1.50 | 1.50 |
| Dist. water | ad 100.00 | ad 100.00 | ad 100.00 |

F3. Anti-Plaque Tooth Cream

|  | I (%) | II (%) | III (%) |
|---|---|---|---|
| Carrageenan | 0.90 | 0.90 | 0.90 |
| Glycerol | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Eucalyptus-spearmint flavouring | 1.00 | 0.60 | 0.20 |
| Menthol-containing composition from Example 1a | 0.125 | 0.56 | 1.00 |
| Sodium dodecyl sulfate | 1.30 | 1.30 | 1.30 |
| Dist. water | ad 100.00 | ad 100.00 | ad 100.00 |

F4. Tooth Cream for the Care of Sensitive Teeth

|  | I (%) | II (%) | III (%) |
|---|---|---|---|
| Na carboxymethylcellulose | 0.70 | 0.70 | 0.70 |
| Xanthan gum | 0.50 | 0.50 | 0.50 |
| Glycerol | 15.00 | 15.00 | 15.00 |
| Sorbitol 70%, in water | 12.00 | 12.00 | 12.00 |
| K nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| Herbal flavouring | 1.00 | 0.60 | 0.20 |
| Menthol-containing composition according to Example 1a | 0.125 | 0.56 | 1.00 |
| Ca carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. water | ad 100.00 | ad 100.00 | ad 100.00 |

F5. Tooth Cream for the Care of Sensitive Teeth

|  | I (%) | II (%) | III (%) |
|---|---|---|---|
| Hydroxyethylcellulose | 1.40 | 1.40 | 1.40 |
| Guar gum | 0.60 | 0.60 | 0.60 |
| Glycerol | 18.00 | 18.00 | 18.00 |
| Sorbitol 70%, in water | 12.00 | 12.00 | 12.00 |
| Na saccharinate | 0.35 | 0.35 | 0.35 |
| Colouring | 0.01 | 0.01 | 0.01 |
| PHB methyl ester | 0.15 | 0.15 | 0.15 |

-continued

|  | I (%) | II (%) | III (%) |
|---|---|---|---|
| PHB propyl ester | 0.04 | 0.04 | 0.04 |
| Sr chloride | 10.50 | 10.50 | 10.50 |
| Cinnamon flavouring | 1.00 | 0.60 | 0.30 |
| Menthol-containing composition from Example 1a | 0.225 | 0.56 | 1.00 |
| Precipitated silica | 15.00 | 15.00 | 15.00 |
| Silicon dioxide | 1.60 | 1.60 | 1.60 |
| Sodium dodecyl sulfate | 1.30 | 1.30 | 1.30 |
| Dist. water | ad 100.00 | ad 100.00 | ad 100.00 |

F6. Ready-to-Use Mouthwash Containing Fluoride

|  | I (%) | II (%) | III (%) |
|---|---|---|---|
| Ethanol | 7.00 | 7.00 | 7.00 |
| Glycerol | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Thymol-wintergreen flavouring | 1.00 | 0.60 | 0.20 |
| Menthol-containing composition from Example 1a | 0.125 | 0.56 | 1.00 |
| Colouring | 0.01 | 0.01 | 0.01 |
| Dist. water | ad 100.00 | ad 100.00 | ad 100.00 |

F7. Mouthwash Concentrate Having Activity Against Halitosis

|  | I (%) | II (%) | III (%) |
|---|---|---|---|
| Ethanol, 95% | 80.00 | 80.00 | 80.00 |
| Na cyclamate | 0.15 | 0.15 | 0.15 |
| Spearmint-thymol flavouring | 3.50 | 3.50 | 3.50 |
| Colouring | 0.01 | 0.01 | 0.01 |
| Menthol-containing composition from Example 1a | 0.50 | 1.0 | 3.0 |
| Dist. water | ad 100.00 | ad 100.00 | ad 100.00 |

F8. Chewing Gum, with Sugar

|  | I (%) | II (%) | III (%) |
|---|---|---|---|
| Chewing gum base | 21.00 | 21.00 | 21.00 |
| Glucose syrup | 16.50 | 16.50 | 16.50 |
| Glycerol | 0.50 | 0.50 | 0.50 |
| Powdered sugar | 60.45 | 60.40 | 60.30 |
| Spearmint flavouring | 1.40 | 1.00 | 0.50 |
| Menthol-containing composition from Example 1a | 0.15 | 0.60 | 1.20 |

F9. Sugar-Free Chewing Gum

|  | I (%) | II (%) | III (%) |
|---|---|---|---|
| Chewing gum base | 30.00 | 30.00 | 30.00 |
| Sorbitol, powder | 38.45 | 38.40 | 38.30 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerol | 1.00 | 1.00 | 1.00 |
| Cinnamon-menthol flavouring | 1.40 | 1.00 | 0.50 |
| Menthol-containing composition from Example 1a | 0.15 | 0.60 | 1.20 |

F10. Chewing Gum Dragées, Sugar-Free

Q1: Constituent Chewing Gum Crude Mass

|  | I (%) | II (%) | III (%) |
|---|---|---|---|
| Chewing gum base | 37.00 | 37.00 | 37.00 |
| Sorbitol, powder | 50.50 | 50.50 | 50.50 |
| Aspartame | 0.20 | 0.20 | 0.20 |
| Plasticiser (Emulgum) | 0.50 | 0.50 | 0.50 |
| Acesulfame K | 0.20 | 0.20 | 0.20 |
| Sorbitol 70% in water | 5.00 | 5.00 | 5.00 |
| Glycerol | 4.00 | 4.00 | 4.00 |
| Peppermint oil flavouring (Optamint ®, Symrise) | 1.60 | 1.60 | 1.60 |
| Menthol, spray-dried | 1.00 | 1.00 | 1.00 |

All the constituents of the chewing gum crude mass (Q1) were mixed, pressed into chewing gum strips and then formed into individual cushion-shaped chewing gum tablets. The cushion-shaped chewing gum tablets were then wetted (gummed) with a 40 wt. % gum arabic solution in a rotating sugar-coating drum. The gummed cushion-shaped chewing gum tablets were subsequently coated with powder mixture A in a rotating sugar-coating drum, mixture A consisting substantially of the menthol-containing solids composition according to the invention and at least one sugar substitute (in most cases selected from isomalt, sorbitol, xylitol, maltitol and/or mannitol, powdered gum arabic can optionally be used in addition). After sufficient drying with cold air, the cushion-shaped chewing gum tablets so coated were dried overnight. For the further application of the coating to the dried, coated cushion-shaped chewing gum tablets using coating solution B, 15 layers were first applied by means of sugar-coating; in the 16th layer, a mixture of constituent C and mixture B is applied. Further layers were then applied using mixture B until the total weight of the coating (Q2) was about 35 wt. % of the weight of the original cushion-shaped chewing gum tablets (Q1). In order to impart gloss to the chewing gum dragées, they were subsequently treated with a glossing agent which consisted of a mixture of equal parts by weight of carnauba wax and beeswax. When chewed, the ready-to-use chewing gum dragées produce in the mouth a new type of menthol taste which is very clear, intense and fresh.

Q2: Constituent Coating (the indicated parts by weight are based on the total weight of the coating (Q2) applied to the cushion-shaped chewing gum tablets (Q1); the total weight of Q2 was about 35%, based on the mass Q1)

|  | I (%) | II (%) | III (%) |
|---|---|---|---|
| Mixture A |  |  |  |
| Isomalt | 0.20 | 0 | 0 |
| Sorbitol | 0 | 0.40 | 0 |
| Mannitol | 0 | 0 | 0.80 |
| Menthol-containing composition from Example 1a | 0.20 | 0.60 | 1.00 |
| Mixture B |  |  |  |
| Isomalt | 68.00 | 67.70 | 67.40 |
| Water | 26.7 | 26.6 | 26.5 |
| Gum arabic, 40% in water (this amount contains the quantity used for gumming) | 2.50 | 2.50 | 2.50 |
| Acesulfame K | 0.05 | 0.05 | 0.05 |
| Aspartame | 0.05 | 0.05 | 0.05 |
| Titanium dioxide | 1.50 | 1.50 | 1.50 |
| Constituent C |  |  |  |
| Peppermint oil flavouring (Optamint ®, Symrise) | 0.80 | 0.60 | 0.20 |

F11. Gelatin Capsules for Direct Consumption

|  | I (%) | II (%) | III (%) |
|---|---|---|---|
| Gelatin coating: |  |  |  |
| Glycerol | 2.014 | 2.014 | 2.014 |
| Gelatin 240 Bloom | 7.91 | 7.91 | 7.91 |
| Sucralose | 0.065 | 0.065 | 0.065 |
| Allura red | 0.006 | 0.006 | 0.006 |
| Brilliant blue | 0.005 | 0.005 | 0.005 |
| Core composition: |  |  |  |
| Vegetable oil triglyceride | 85.0 | 80.0 | 73.0 |
| Flavouring B | 4.0 | 6.0 | 10.0 |
| Menthol-containing composition from Example 1a | 1.0 | 4.0 | 7.0 |

Flavouring B had the following composition (amounts are each in wt. %): 0.1% neotame powder, 0.05% aspartame, 29.3% lemon oil, 29.3% orange oil, 2.97% sucralose, 2.28% triacetin, 5.4% diethyl tartrate, 12.1% peppermint oil Yakima, 0.7% ethanol, 3.36% 2-hydroxyethylmenthyl carbonate, 3.0% 2-hydroxypropylmenthyl carbonate, 0.27% vanillin, 5.5% D-limonene, 5.67% L-menthyl acetate.

The gelatin capsule suitable for direct consumption had a diameter of 5 mm, and the weight ratio of core material to coating material was 90:10. The capsule opened in the mouth within a period of less than 10 seconds and dissolved completely within a period of less than 50 seconds.

F12. Chewy Sweet

| Water |  | 7.5% |
|---|---|---|
| Sugar | refined sugar C4 | 41.2% |
| Glucose syrup | dextrose 40 | 36.2% |
| Hardened vegetable fat | melting point 32-36° C. | 6.5% |
| Lecithin | emulsifier (soya lecithin) | 0.3% |
| Gelatin | porcine gelatin | 0.8% |
| Fondant | type-S30 | 4.8% |
| Lemon flavouring |  | 0.6% |
| Menthol-containing composition from Example 1a |  | 2.1% |

Notes on Preparation:
a) allow the gelatin to swell in water (1.8 times the amount of gelatin) at 70° C. for 2 hours;
b) boil the sugar, syrup, water, fat and lecithin at 123° C.;
c) slowly mix the gelatin solution with the boiled mixture;
d) stir in the menthol-containing composition and optional colouring;
e) adjust the resulting mass to a temperature of about 70° C. on a cooling table, then add the fondant and expose to air for about 3 minutes on a drawing machine;
f) then cut and pack the chewy sweet mass.

When the chewy sweet is consumed, a strong menthol taste is perceived during chewing, the texture of the chewy sweet is pleasant.

F13. Compressed Product, with Sugar or Sugar-Free

| Dextrose (with sugar) or sorbitol (sugar-free) |  | 98.5-98.8% |
|---|---|---|
| Magnesium stearate | glidant | 1.0% |
| Menthol-containing composition from Example 1a |  | 0.2-0.5% |

Mix all the constituents and press the mixture in a suitable machine to form compressed products.

F14. Extrudate

| Glucose syrup, spray-dried (DE value: 31-34) | Glucidex IT33W (Roquette) | 60.0% |
|---|---|---|
| Maltodextrin (DE value: 17-20) | (Cerestar) | 26.0% |
| Emulsifier Monomuls | emulsifier based on hardened palm oil; melting point: 64° C., (Grünau) | 1.5% |
| Dextrose monohydrate (DE value: 99.5) | dextrose, containing water of crystallisation (Cerestar) | 1.5% |
| Water |  | 1.5% |
| Menthol-containing composition from Example 1a |  | 9.5% |

Notes on Preparation (See Also WO 03/092412):

All the constituents were mixed and fed by single-point metering into a twin-screw extruder. The extrusion temperatures were from 100 to 120° C., the specific energy input was 0.2 kWh/kg. Immediately upon leaving the nozzles, the strands emerging from the extruder nozzle plate having 1 mm bores were cut by means of rotating blades into particles having a diameter of about 1 mm. The granules so prepared had a menthol content of 10 wt. %.

The invention claimed is:
1. A menthol-containing solids composition comprising:
(a) a solid menthol component including bodies having a menthol content of 95 wt. % or more, based on the total weight of the bodies, and
(b) a solid particulate silicon dioxide component having a particle size of not more than 100 μm, wherein particles of the silicon dioxide component are adhered to the surface of the bodies of the menthol component by mix- ing said solid menthol component with said solid particulate silicon dioxide, and
wherein the amount of the silicon dioxide component is not more than 4 wt. % and the amount of the solid particulate menthol component is at least 95 wt. %, in each case based on the total weight of the solids composition.

2. The menthol-containing solids composition according to claim 1, wherein the bodies of the solid menthol component include from 0 to 1% of inorganic constituents, based on the total weight of the bodies.

3. The menthol-containing solids composition according to claim 1, wherein the bodies of the solid menthol component are in the form of crystals, prills, flakes, pressed articles, pastilles, granules, powder and/or dust.

4. The menthol-containing solids composition according to claim 1, wherein the bodies of the solid menthol component do not contain surfactants and/or peppermint oil on a surface thereof and/or include not more than 0.2 wt. % water, based on the total weight of the solids composition.

5. The menthol-containing solids composition according to claim 1, wherein the particles of the silicon dioxide component include precipitated silica and/or pyrogenic silicon dioxide.

6. The menthol-containing solids composition according to claim 1, wherein particles of the silicon dioxide component adhere to and cover a surface of the bodies of the solid menthol component wherein the sublimation capacity or vapour pressure of the menthol from the bodies of the solid menthol component at 25° C. and 1013 mbar is reduced by at least 25% compared with the pure menthol component (a).

7. The menthol-containing solids composition according to claim 1, wherein the amount of the silicon dioxide component in the solids composition is not more than 2.5 wt. %, based on the total weight of the solids composition.

8. The menthol-containing solids composition according to claims 1, wherein the solids composition is used in an article selected from the group consisting of: products suitable for consumption; smoking products, tobacco products, perfumes (fragrance mixtures), flavouring mixtures, oral hygiene products, cosmetic, pharmaceutical and dermatological products, encapsulated menthol-containing solids compositions.

9. A sugar-coated product suitable for consumption having a coating, wherein at least one layer of the coating comprises the menthol-containing solids composition according to claim 1.

10. A method for preparing the menthol-containing solids composition according to claim 1, comprising the step of:
mixing (a) a solid particulate menthol component including solid bodies having a menthol content of 95 wt. % or more, based on the total weight of the bodies, and (b) a particulate solid silicon dioxide component having a particle size of not more than 100 μm, until particles of the silicon dioxide component adhere to a surface et the bodies of the menthol component, wherein
the amount of the silicon dioxide component is not more than 4 wt. % and the amount of the menthol component is at least 95 wt. %, in each case based on the total weight of the prepared solids composition.

11. The menthol-containing solids composition of claim 1, wherein said composition contains not more than 0.2 wt % water.

12. The menthol-containing solids composition of claim 1, wherein said solid bodies of said menthol component are free of silica particles inside the bodies.

13. The menthol-containing solids composition of claim 12, wherein said menthol-containing solids composition is free of surfactant residues and have a content of not more than 0.2 wt % based on the total weight of the composition.

14. The method of claim 10, wherein the solid menthol component and the particulate silicon dioxide component are introduced to a mixer and dry mixed adhere the silicon dioxide component to the menthol component.

15. The method of claim 10, wherein said menthol-containing solids composition has a water content of not more than 0.2 wt %.

16. The menthol-containing solids composition of claim 1, wherein said solid bodies have a menthol content of 98-99.8 wt. %, based on the total weight of the bodies.

17. The menthol-containing solids composition of claim 1, wherein said bodies have no silicon dioxide within the bodies.

* * * * *

UNITED STATES PATENT AND TRADEMARK OFFICE
CERTIFICATE OF CORRECTION

PATENT NO.         : 8,524,257 B2                                          Page 1 of 1
APPLICATION NO.    : 11/908653
DATED              : September 3, 2013
INVENTOR(S)        : Reinhard Nowak et al.

It is certified that error appears in the above-identified patent and that said Letters Patent is hereby corrected as shown below:

In the Claims

In column 22, line 27, of claim 13 reads "free of surfactant residues and have a content of not more than" should read "free of surfactant residues and have a water content of not more than"
In column 22, line 31, of claim 14 reads "introduced to a mixer and dry mixed adhere the silicon diox-" should read "introduced to a mixer and dry mixed to adhere the silicon diox-"

Signed and Sealed this
Tenth Day of December, 2013

Margaret A. Focarino
*Commissioner for Patents of the United States Patent and Trademark Office*